(12) United States Patent
Babcock et al.

(10) Patent No.: US 9,835,614 B2
(45) Date of Patent: Dec. 5, 2017

(54) MEASUREMENT OF CELL GROWTH AND DRUG SUSCEPTIBILITY BY RESONANT MASS MEASUREMENT

(71) Applicant: Affinity Biosensors, LLC, Santa Barbara, CA (US)

(72) Inventors: Ken Babcock, Santa Barbara, CA (US); Cynthia Schneider, Santa Barbara, CA (US)

(73) Assignee: Affinity Biosensors, LLC, Santa Barbara, CA (US)

(*) Notice: Subject to any disclaimer, the term of this patent is extended or adjusted under 35 U.S.C. 154(b) by 0 days.

(21) Appl. No.: 14/480,078

(22) Filed: Sep. 8, 2014

(65) Prior Publication Data

US 2015/0072373 A1 Mar. 12, 2015

Related U.S. Application Data

(60) Provisional application No. 61/875,248, filed on Sep. 9, 2013.

(51) Int. Cl.

| | | |
|---|---|---|
| *C12Q 1/02* | (2006.01) | |
| *C12Q 1/28* | (2006.01) | |
| *C12M 1/34* | (2006.01) | |
| *G01N 33/50* | (2006.01) | |
| *C12Q 1/18* | (2006.01) | |
| *G01N 15/10* | (2006.01) | |
| *G01N 33/543* | (2006.01) | |
| *G01N 27/447* | (2006.01) | |

(52) U.S. Cl.
CPC .......... *G01N 33/5011* (2013.01); *C12Q 1/18* (2013.01); *G01N 15/10* (2013.01); *G01N 27/447* (2013.01); *G01N 33/54373* (2013.01); *G01N 2015/1006* (2013.01); *G01N 2015/1043* (2013.01); *G01N 2500/04* (2013.01)

(58) Field of Classification Search
CPC .............. G01N 33/5011; G01N 15/10; G01N 2015/1043; G01N 2500/04; C12Q 1/18
USPC .................... 435/29, 32, 288.7, 288.5, 287.1
See application file for complete search history.

(56) References Cited

U.S. PATENT DOCUMENTS

| | | | |
|---|---|---|---|
| 8,087,284 B2 * | 1/2012 | Babcock | .................. G01N 5/00 73/32 A |
| 8,312,763 B2 | 11/2012 | Manalis | |
| 8,722,419 B2 | 5/2014 | Manalis et al. | |
| 2009/0044608 A1 | 2/2009 | Babcock et al. | |
| 2010/0297747 A1 | 11/2010 | Manalis et al. | |
| 2012/0174657 A1 | 7/2012 | Babcock et al. | |

OTHER PUBLICATIONS

Son et al. Direct Observation of Mammalian Cell Growth and Size Regulation; Nature Methods, vol. 9 (Aug. 5, 2012) pp. 1-4.*
Bryan et al. Measurement of Mass, Density and Volume During the Cell Cycle of Yeast; Proceedings of the National Academy of Science, vol. 107, No. 3 (2010) pp. 999-1004.*
Godin et al. Using Buoyant Mass to Measure the Growth of Single Cells; Nature Methods, vol. 7, No. 5 (2010) pp. 387-392.*

* cited by examiner

*Primary Examiner* — Scott Long
*Assistant Examiner* — Paul Martin
(74) *Attorney, Agent, or Firm* — Mark Rodgers

(57) ABSTRACT

System and Method for measuring the growth of a bacterial culture and its response to one or more antimicrobials using measurement of mass of individual microbes. Methods include periodic sampling, determining change in mass and concentration, and comparing growth rates of cultures in nutrient broth vs. mixtures containing various antibiotic mixtures. A number of antimicrobials can be compared in one measurement by multiplexing or using multiple sensors to measure in parallel. Growth and antibiotic efficacy can be assessed at low concentrations at the onset of growth, typically within 1 to 2 hours.

23 Claims, 6 Drawing Sheets

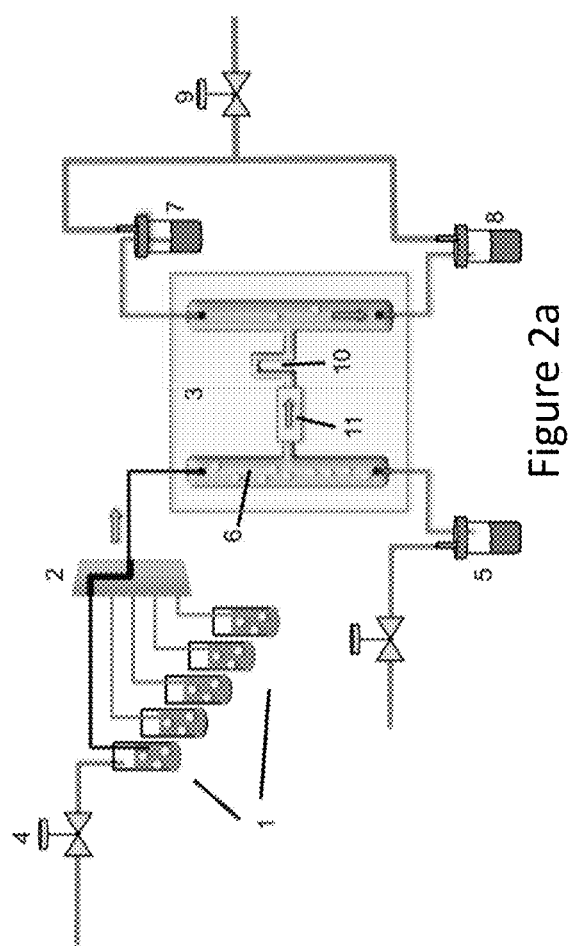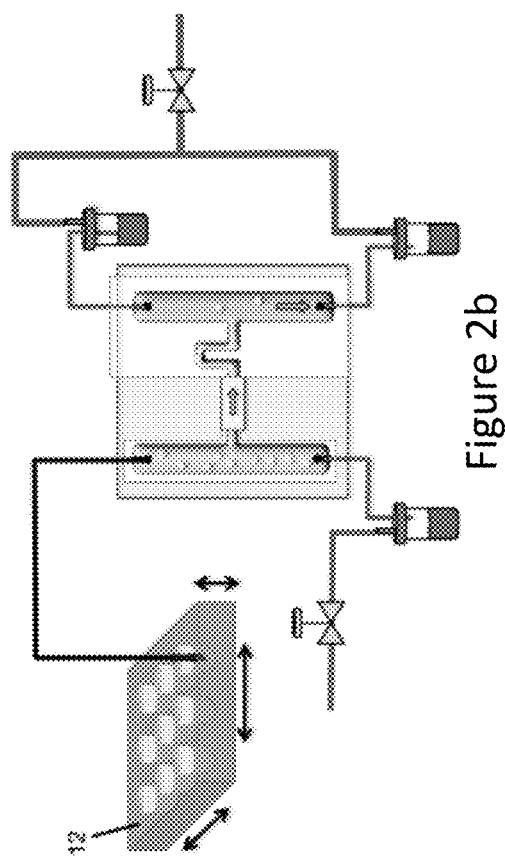

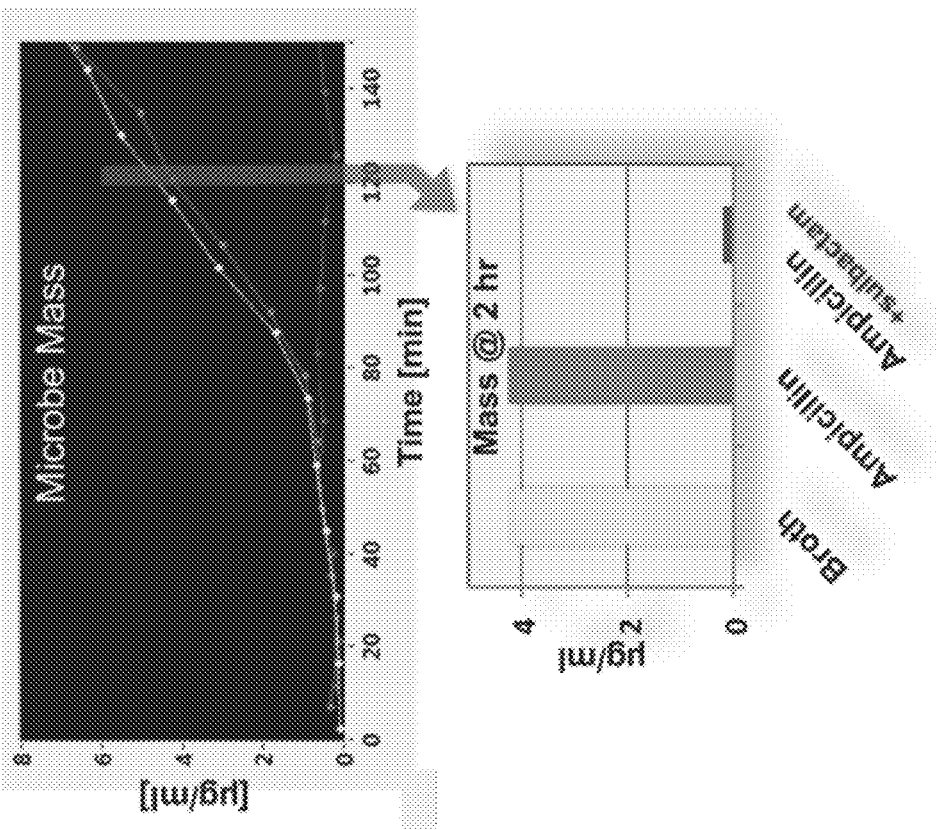

MEASUREMENT OF CELL GROWTH AND DRUG SUSCEPTIBILITY BY RESONANT MASS MEASUREMENT

RELATED APPLICATIONS

This application claims priority to U.S. Provisional Application Ser. No. 61/875,248, filed Sep. 9, 2013

FEDERALLY SPONSORED RESEARCH

N/A

BACKGROUND AND SUMMARY

This application relates to measurements of cell growth, and in particular in the presence of drugs or other growth affecting agents, when the cells with or without the agents are flowed through a fluid channel embedded in, or attached to, a resonant structure.

This disclosure in some embodiments teaches a method and a system for rapidly measuring the effect of antibiotics on the growth of a bacterial culture, as well as other applications related to the counting and/or determining the mass/size of particles in the mass range of a few femtograms and larger, in the presence of growth-affecting agents. The disclosure addresses a strong diagnostic need to assess antibiotic efficacy in at most a few hours. A bacteria culture, or other cell culture, suspended in a liquid broth, may be passed through a mechanically resonating structure such as a suspended microchannel of appropriate size. A plurality of individual microbes may be detected and, optionally, their mass measured, by the effect their mass has on the microchannel's resonant frequency as they pass through the channel, one by one. This effect is described in the art as a method of measuring particle characteristics such as mass and size (U.S. application Ser. No. 13/310,776 and related applications incorporated by reference) and forms the basis for certain commercial particle measurement instruments. Additionally, the flow rate and measured sample volume can be determined from the time of passage of the microbes through the resonant microchannel, or by independent measurements of flow rate. Thus, the culture's distribution of microbe mass and concentration (microbes per ml of culture medium) may be measured.

To determine growth rate, the culture may be sampled at intervals, typically a few minutes apart. In each such time interval, multiple microbes may be detected and measured, providing information about the current number concentration of the microbes and the distribution of their masses. Performing these measurements over successive time intervals reveals the time development of the concentration and microbe mass and gives a detailed profile of the culture's growth rate and characteristics.

The above measurements can be performed on cultures containing antibiotics of various types and concentrations. The response of the culture to a particular antibiotic mixture can be determined by comparing the culture growth rate to an "unexposed" culture (a "control" sample) containing no antibiotics. Microbes whose growth is inhibited by an antimicrobial will show growth well below that of the unexposed culture, whereas a microbe strain that is "resistant" to the antimicrobial will show robust growth. A simplified, endpoint version of the method compares the mass and concentration measurements of the unexposed culture and the antibiotic mixture at a specified time after the start of the cultures' growth.

Finally, the disclosure in some embodiments teaches how the effect of a number of antibiotics can be assessed in one measurement by sequentially sampling from different mixtures in successive time intervals, or by simultaneously measuring different mixtures by using multiple resonant mass detectors.

This method of monitoring growth rate and comparison of growth rate between samples can be generalized beyond bacteria to assess the growth rate of any living cells or microscopic organisms, such as fungi, protozoa, and mammalian cells, including cancerous cells, and to measure the effects of drugs on their growth rate.

In addition to drugs, the effects of other agents on cell growth can also be assessed by this method, including topical anti-infectives and bacteriocides, anti-bacterial soaps, fungicides, and cosmetics.

This method can also be used to assess growth rate in applications where the goal is to promote growth, rather than inhibit it. An example is a comparison of the effectiveness of nutrient broths designed to optimize growth of cell cultures used, for example, to produce proteins used in biotherapeutic drugs, or to maximize growth rate in cultures of algae used for biofuels.

BRIEF DESCRIPTION OF THE DRAWINGS

FIGS. 2a and 2b show alternative measurement systems that allow the growth rate of several cultures to be measured and compared.

FIG. 6a and FIG. 6b shows (a) mass growth curves and (b) mass content values at 120 min. derived from the E. coli data in FIG. 4.

DETAILED DESCRIPTION

Figure 1A:
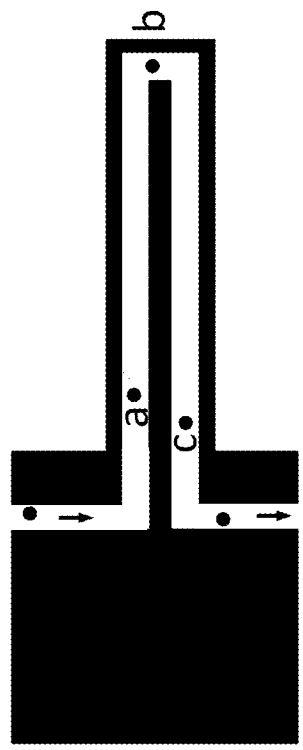
FIGS. 1a and 1b show a microchannel resonator, in which a microfluidic channel is embedded in a mechanically resonant structure such as a cantilever. 1a) cutaway view shows microbes suspended in fluid passing through the microchannel inside a mechanically resonant cantilever. 1b) shows the response of the resonant frequency as a microbe passes through it.

This application in some embodiments discloses a method and a system for measuring the effect of antimicrobials on the growth of bacteria using a sensor able to detect microbes and measure their mass to high precision. FIG. 1a shows an example of a mass sensor, in this case a microfluidic channel embedded in a mechanically resonant structure. In this example, the structure is a cantilever whose free end can oscillate in a vertical direction (in the figure, in and out of the plane of the page). The structure can be driven to resonate as the fluid passes through it. Such sensors are described in the incorporated references, and can be fabricated with precise micron- and sub-micron scale dimensions using micro-electrical mechanical systems (MEMS) fabrication techniques. Examples include sensors used in commercially available particle measurement instruments which have dimensions between 20 and 300 μm long, with channels having apertures from submicron dimensions up to 30 μm or more. These sensors are known in the literature as suspended microchannel resonators (SMR), and the method of measuring particle mass and other properties is known as resonant mass measurement. Suitable SMR sensors resonate in a frequency range from 20 kHz to more than 2 MHz, and instrumentation has been developed to measure their resonant frequency with precisions of a few parts per billion at a bandwidth of 1 kHz. While the quantitative characteristics described here are typical of currently available sensors, the measurement principle is not limited to these values, and the method can encompass a wider range of sensor sizes, resonant frequencies, and other characteristics. In addition, resonant structures other than cantilevers can be fabricated to resonate, including a beam containing a microfluidic channel suspended at both ends, and plate-shaped resonators that accommodate fluid flow.

Figure 1B:
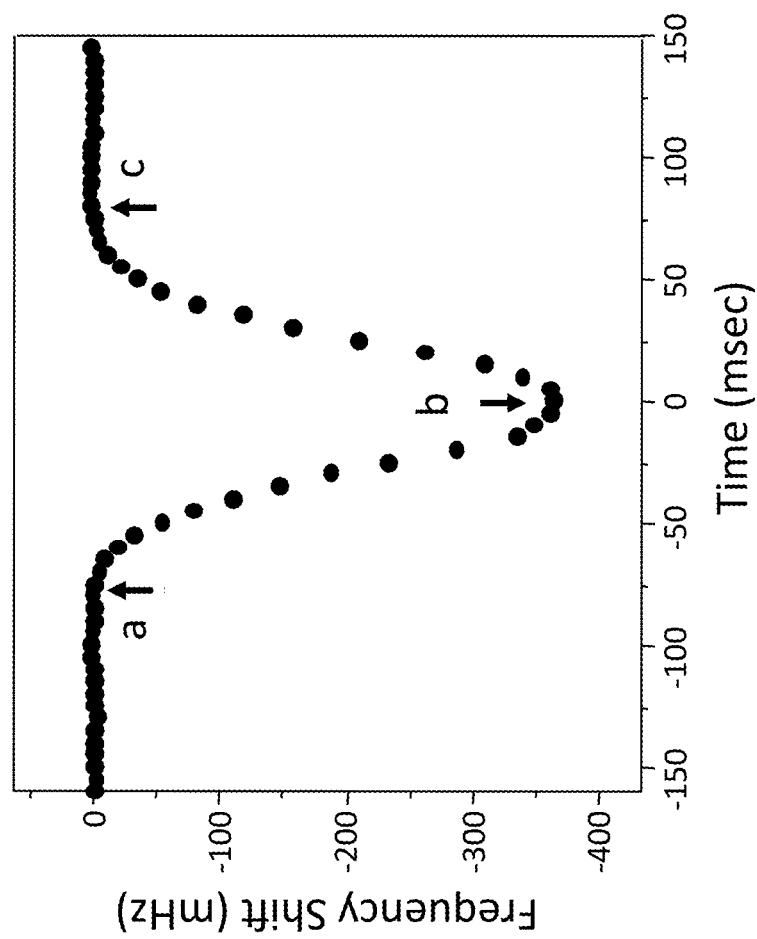

FIG. 1b) shows a representative time evolution of frequency measurements when a particle suspended in fluid passes through the resonant portion of the microchannel. The corresponding positions of the particle in the resonator to the frequency vs. time plot are indicated a, b, and c. Because the particle displaces the fluid in the resonator, if its density is greater than that of the fluid, the overall mass of the resonator increases as the particle passes through it. This causes the sensor resonant frequency to decrease, then return to its baseline value when the particle exits the sensor. The relation between the particle buoyant mass (i.e., the mass of the particle above that of the fluid it displaces) and the change in resonant frequency can be calibrated using, for example, particle standards having known size and mass. Particle measurement instruments based on such sensors measure the frequency excursions of a series of particles as they pass through the sensor, and from this determine the masses and other physical properties of the particles.

For such measurements, and for the measurements described in the embodiment below, the particle concentration (number of particles per unit volume of fluid) is assumed to be low enough that, for the great majority of the time, at most one particle is present in the sensor at any given time. This condition can be stated approximately in that the particle concentration should be less than the reciprocal of the volume of the active portion of the resonant mass sensor. A typical sensor used for microbial measurements has an active volume of about 25 picoliters, with a corresponding upper concentration limit of about $4 \times 10^7$ microbes/ml. If needed, higher concentrations can also be addressed by using sensors with smaller volumes.

Operating the SMR or other resonant mass sensor in this fashion accomplishes two important things. First, the presence of one particle at a time in the measurement region of the system allows for accurate measurement of the particles' masses. Thus, if many particles or cells pass through the sensor serially over time, the average mass of a number of particles or cells may be measured in selected time intervals, providing a highly accurate measure of the growth or diminishment of cell mass over time. Similarly, if the number of cells per unit volume (concentration) increases i.e., replication takes place, the number of particle passing through the sensor per unit time will change as well. Thus the sensor operated suitably is both a highly accurate mass sensor as well as a highly accurate counter, allowing for accurate measurement of changes in cell mass and in cell concentration. Both of these capabilities are achieved in various embodiments.

SMRs having properties suitable for measuring the mass of bacteria have been fabricated. For example, a microchannel having an aperture of about 8 μm accommodates most bacteria strains, whose individual microbes typically range from about 1 to a few μm. In addition, the net density of a microbe is greater than that of water or of nutrient broth, allowing its "buoyant mass", i.e., the mass of the microbe over that of the fluid it displaces, to be detected and measured. As a specific example, typical *E. coli* strains have a buoyant mass between 100 and 500 fg when suspended in a nutrient broth such as Lurea broth. This mass is readily measurable by SMR's of appropriate size, which have a buoyant mass lower limit of detection near 1 fg.

To measure the contents of a bacteria culture, the mass sensor is configured in a fluid system such as shown in FIG. 2a, which facilitates the loading of the bacteria culture into the mass sensor and controlling flow during measurement. The cultures and antibiotic mixtures to be measured are contained in the sample vials (1) of which there may only be one for some embodiments. The sample vials may be immersed in a temperature-controlled water bath (not shown) so that growth may be assessed at physiological or other desired temperatures. A selection valve (2) allows a portion one of the samples to be drawn from and directed to the sensor assembly (3). The sensor assembly may include, for example, a single MEMS-fabricated die, or "chip", comprising the resonant mass sensor as well as microfabricated fluidics features such as channels and ports that interface to the rest of the system. As shown, culture in the first vial is selected. A head pressure that is regulated with pressure regulator (4) is applied to the selected vial. In a loading phase, the waste vial (5) is vented. The head pressure in the sample vial forces fluid to flow out of the connecting fluidic tubing (blue) and into a reservoir channel (6) on the sensor assembly. The cross sectional area of the reservoir channel is sufficiently large that the flow rates can be relatively large during this loading phase and the reservoir can be loaded quickly, typically in a few seconds. Once the reservoir channel is filled with sample fluid, the same pressure is applied to waste vial (5). Because the sample and waste vials both experience the same pressure, flow through the reservoir channel is then stopped.

In a measurement phase, pressures are applied to a reference vial (7), which may contain water or other solutions, and to the corresponding waste vial (8), using pressure regulator (9). During measurement, the pressure applied by regulator (9) is set to be slightly less than the pressure applied to the sample vial (2) and waste vial (5). This creates a forward pressure through the active, resonant portion of the sensor (10), and the sample flows through it at a controlled rate. The resonant frequency of the sensor is monitored during this phase to detect and measure the mass of individual microbes flowing through it, as described above. The flow rate through the sensor can be measured simultaneously with a flow meter (11) so that the volume of sample can be monitored.

This embodiment incorporates a flow meter fabricated onto the sensor assembly. One example of such a sensor is a CMOS-based structure that monitors small temperature difference in the fluid (see, for example, commercial flow meters from Sensirion). The system may employ alternative ways of setting or monitoring flow rate. For example, syringe pumps could deliver the sample at a known flow rate, and can also be used instead of pressured regulators and pressure heads. Another method of determining flow rate is to measure the time of transit of particles through the active portion of the sensor. Combining this information with the known volume of the sensor provides an excellent measure of flow rate. This method is employed in commercial instruments that measure particle size. Other flow control means known in the microfluidic art may be employed as well. FIG. 2b illustrates an alternative system where the multiple sample vials or wells are in an array (12) which is positioned with staging to present the culture contained in any desired well to the fluidic system. In either case, the process may be repeated for a portion of culture, from selected vials or wells, at a second time, the measurements repeated, and the change corellated with cell growth in the selected vials wells between the two times.

Figures 3A, 3B, 3C:
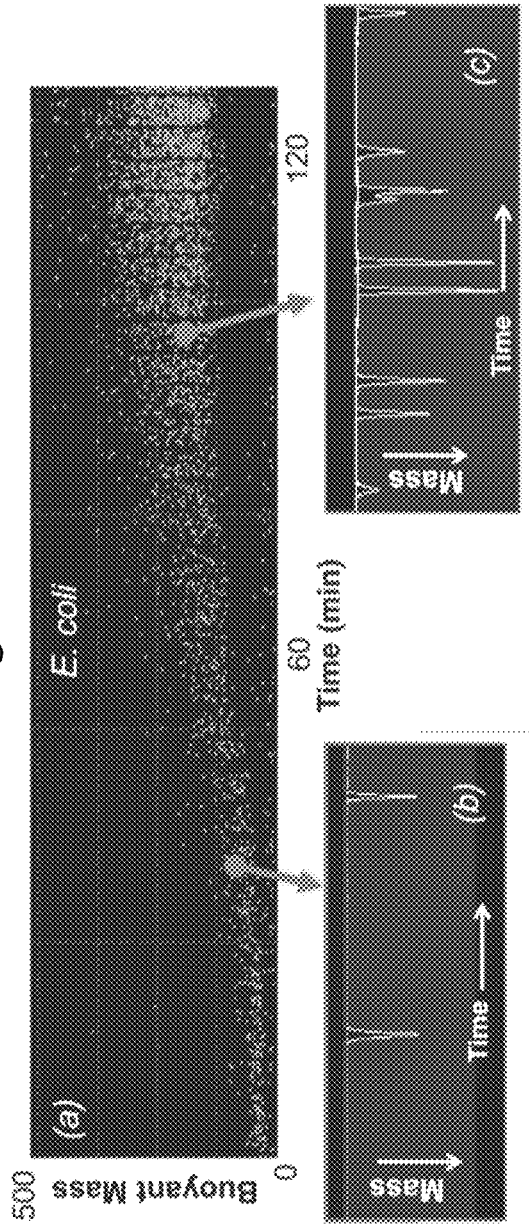
FIGS. 3a, 3b and 3cs show measurements E. coli taken at successive time intervals. 3(a), each dot shows the buoyant mass of each microbe and when it was measured. 3(b), (c) Real-time signals from the resonant mass sensor.

FIG. 3 shows the measurement of an E. coli strain. In FIG. 3(a), each red dot represents the buoyant mass of an individual microbe, measured as it passed through the mass sensor. The FIGS. 3(b) and 3(c) show time traces of the sensor resonant frequency. Each downward peak is caused by a microbe, and the magnitude of the peak provides a measure of its buoyant mass. To follow the time development of this culture, the measurement was paused every five minutes and fresh sample loaded from the sample vial, followed by measuring for another five minutes. The pauses during sample loading are visible in FIG. 3(a) as narrow bands absent of particles. The time evolution of the culture is revealed by changes in the measurements performed in successive five minute intervals. About half way through this example, the concentration of the culture begins to increase rapidly as the E. coli replicate and double in number approximately every 20 minutes as they proceed through their cell cycle. The inset FIG. 3(c) also illustrates this with more rapid arrival of the microbe "peaks" than the earlier time trace 3(b). A powerful aspect of this method is that the concentration of the culture can be measured very early in its time evolution, when the microbe concentration is low (as few as $10^3$/ml).

Figure 4:
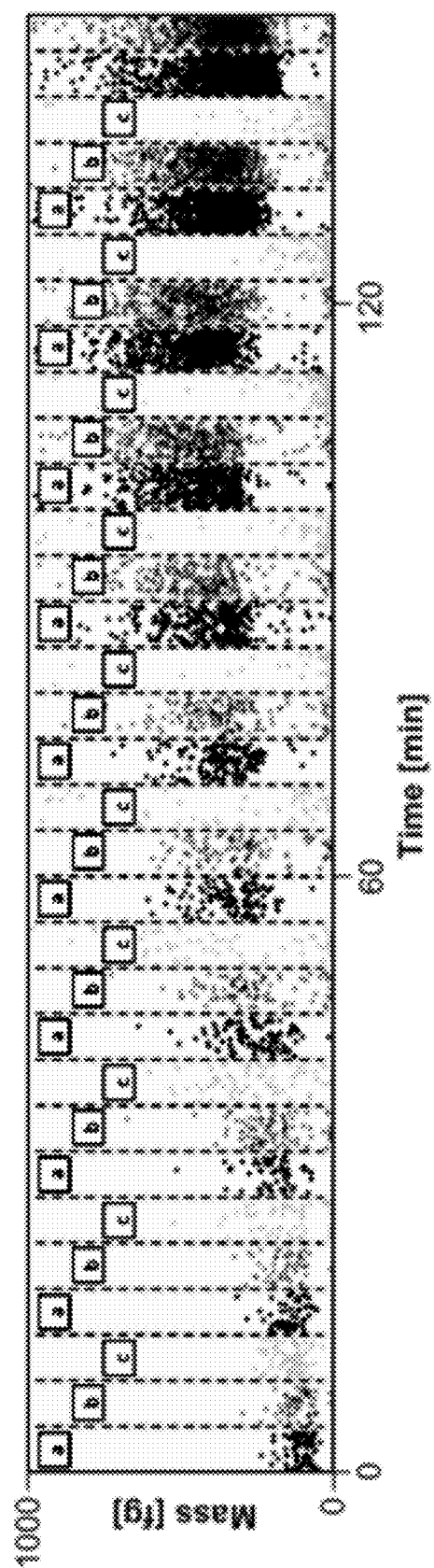
FIG. 4 shows measurements of three cultures containing E. coli over several time intervals made by selecting each culture sequentially using a selection valve.

Multiple cultures can be measured simultaneously over time by using a selection valve as shown in FIG. 2. FIG. 4 shows measurement of three cultures containing E. coli by "multiplexing" the load and measurement phases for the three vials cyclically. Each gray scale level represents data from one of the cultures. The darkest data points, in the time intervals labeled "a", are data are for a culture of E. coli in nutrient broth; the intermediate dots ("b" intervals) are data are for a culture in broth containing 64 µg/ml of the antibiotic ampicillin; and the lights dots ("c" intervals) data are for a culture in broth containing 64 µg/ml of ampicillin augmented with the compound sulbactam. Each mixture was inoculated with approximately the same number of live E. coli microbes just prior to the measurement. The time development clearly shows that the mass and number of microbes in the first two cultures ("a" and "b") grow robustly, while in the third culture ("c") they do not. The masses of the microbe in the third culture in fact decrease, reflecting the action of the ampicillin/sulbactam on interfering with cell wall growth and eventually causing the microbes to fall apart into low mass debris. Diagnostically, these data confirm that this strain of E. coli is resistant to ampicillin at the measured concentration, but that the addition of sulbactam overcomes this resistance and inhibits growth.

Alternate system configurations can be used to analyze multiple cultures. For example, the cultures in the various wells in the array in FIG. 2b can be sampled sequentially within a time interval, and a "multiplexed" measurement performed as with the selection valve used in the previous embodiment. Alternatively, to increase throughput, multiple microchannel sensors may be used in parallel, with each sensor dedicated to measurement of one or a subset of the cultures to be measured.

Also, the number of cells can also be used to determine growth, by concentration and or cell volume. The mass sensor as well as optical sensors may yield presence and number information as well as flow rate, all of which can be related to growth to cells and/or cell volume per unit volume. Such techniques related to fluid/particle mixtures in microchannels are described in co-pending, earlier filed U.S. application Ser. No. 14/259,773, assigned to the same assignee, which is incorporated by reference in its entirety.

Figures 5A, 5B:
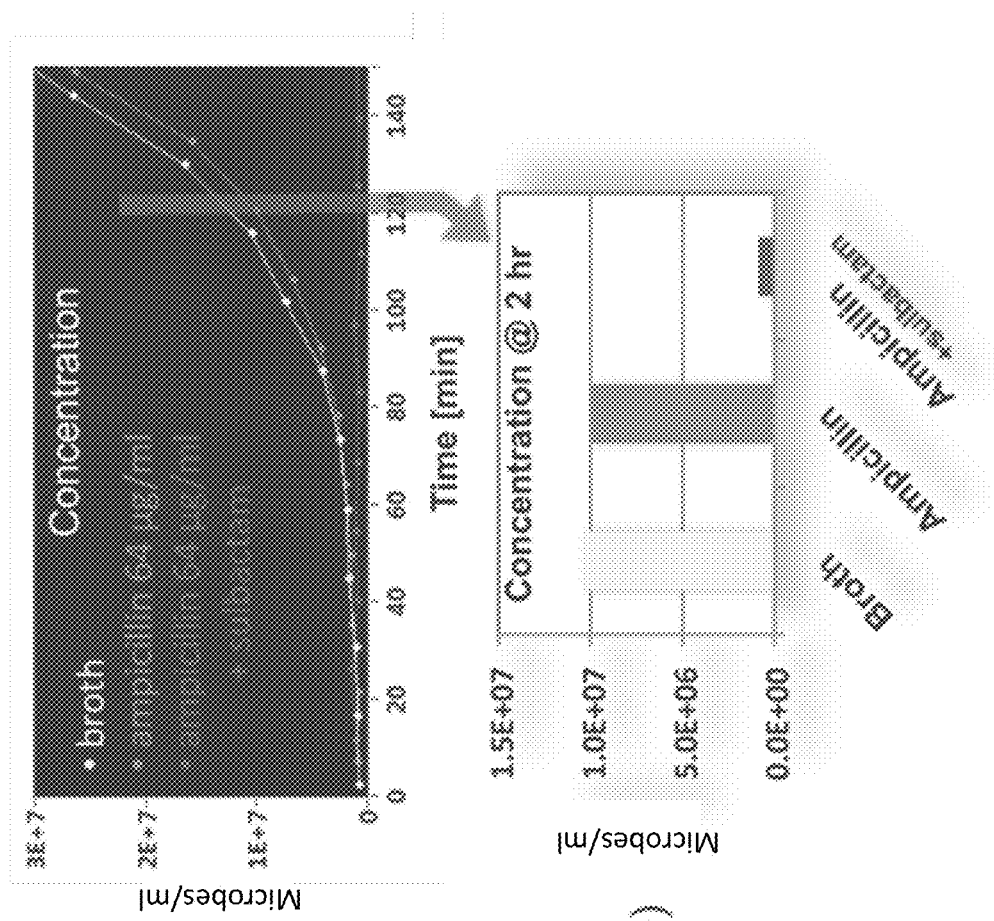
FIG. 5a and FIG. 5b shows (a) concentration growth curves and (b) concentration values at 120 min. derived from the E. coli data in FIG. 4.

The "raw" data of FIG. 4 can be reduced to growth curves by calculating the microbe number concentration in each time interval, as shown in FIG. 5(a). The result shows quantitatively the increase in microbe concentration (the number of microbes per ml) that begins at about one hour for both the nutrient broth ("a" data points) and broth/ampicillin ("b" data points) cultures. In contrast, the microbe concentration never increases for the ampicillin/sulbactam mixture ("c" data points).

The data can be further reduced to an "endpoint" measurement by comparing the state of all three cultures at a single point in time. An example is shown in FIG. 5(b), which compares the microbe concentrations after two hours, and again confirmed that the ampicillin/sulbactam mixture inhibited growth. This represents a simple version of a measurement that usefully compares the efficacy of an antimicrobial.

In addition to concentration growth curves, the evolution of mean microbe mass vs. time (units g or fg), and the total mass content, i.e., microbe mass per unit volume (units µg/ml) can also be plotted vs. time as a measure of growth. FIG. 6(a) shows mass content growth curves for the data in FIG. 4. To obtain this plot, for every measurement interval, the masses of all microbes measured in that interval were summed, and the result divided by the volume of sample that passed through the mass sensor during the interval. These growth curves again confirm the general growth characteristics of the three cultures, but such alternate representations can also provide additional useful data. For example, the mass content of the ampicillin/sulbactam mixture increased slightly over the first 90 minutes, then decreased significantly. Combined with the concentration data FIG. 5(a), this indicates that the mean mass of the E. coli initially increased in this culture, while their number did not, i.e., they did not replicate. The later decrease in mass content reflects the disintegration of the cell walls. FIG. 6(b) shows endpoint measurements for the microbe mass content of the mixtures.

The ability to independently monitor number concentration and microbial mass can be important in some diagnostic scenarios. For example, in response to antibiotics, some bacteria strains increase their mass while slowing their cell cycle and corresponding rate of replication, e.g., certain carbepenem-resistant strains of Klebsiella pneumoniae in the antibiotic imipenem. These effects can be distinguished and show that cell division is inhibited, whereas conventional methods such as light obscuration can confuse the increase in microbial size with an increase in number concentration.

In some embodiments, growth is typically measurable as soon as the microbes begin replicating. In most culture-based measurements, a small amount (between 1 and 100 µl) of a mature culture or patient sample is added to a few ml of the broth and antibiotic mixtures—i.e., the mixtures are "inoculated" with the target bacteria. The resulting inoculated mixtures may have a relatively low concentration of microbes, in the range $10^3$-$10^6$/ml. These concentrations are below the values detectable by conventional means such as OD measurements, but may be detected and measured in some of the disclosed embodiments.

The ability to measure culture content at low concentrations is enabled by the ability to detect and measure individual microbes, which is in turn enabled by the very high sensitivity of the resonant mass sensors. In addition, the buoyant mass limit of detection for typical SMR sensors is near 1 fg, which is less than 1% of the buoyant mass of a typical microbe such as *E. coli*. This level of sensitivity means a wide range of strain of microorgism strains may be measured, and the masses of the individual microbes measured precisely.

When first added, the inoculant bacteria may be in a "lag phase" in which their metabolic activity is low, and they do not immediately begin replicating. For example, the growth curves in FIG. 4 show increases in concentration after about one hour. Once replication does begin, increases in concentration may be detected quickly. The result is that, in most microbe/antibiotic mixtures, growth can be assessed within two hours of inoculation.

In contrast, conventional methods based on measuring growth in broth typically require a wait time, or pre-measurement incubation time, that goes beyond even the culture's lag phase, and requires the microbes to under replication for an extended period and it reaches a sufficiently high concentration that it can be measured and growth assessed. For example, in automated instruments that use transmitted light to measure optical density ("OD") to determine antibiotic susceptibility, the growth is typically not measured until after a wait time of 8 to 16 hours. In some of the disclosed embodiments this pre-measurement incubation time is eliminated, and growth can be assessed very soon after replication begins. The overall measurement time is limited primarily by the duration of the bacteria lag phase. Tests indicate that the growth response to various mixtures can be assessed in a couple of hours and the results agree with the results from established, conventional methods that can take many hours longer.

The above discussion of measurement of multiple samples showed the response of the same microbe strain to three different antibiotic mixtures. The method could be extended to larger numbers of mixtures; to comparing growth of a microbe strain to an antibiotic at different concentrations; to comparing the response of different microbe strains to an antibiotic; or any combination of these factors.

The measurement method and system taught herein can tolerate a wide range of initial microbe concentration, so long as they are below the maximum measurable concentration (approximately 1/sensor volume, as discussed above). So long as this condition is met, the starting concentration does not have to be known before the measurement because it will established by the measurement at the start. Also, when measuring multiple mixtures, the initial concentrations do not have to be equal, since growth for any particular mixture can be assessed relative to its starting value. This flexibility is useful in realistic scenarios where the history or precise state of a culture or patient sample may not be known.

Another beneficial feature is that the measurements give a good statistical assessment of the state of a culture and its development in time. This is because, in any given time interval, numerous cells are typically measured. For example, for typical SMR sensors and flow rates, hundreds of cells can be measured in a few minutes even at relatively low concentrations near $10^6$/ml, and in robustly growing cultures the number may be thousands, numbers that are sufficient to determine the number concentration and mean microbe mass with good precision. The ability to measure a representative selection of microbes also allows valid measurements to be made when there is a secondary, minor-strain population present in the culture. In some cases the secondary strain may not respond to the mixture in the same way as the majority strain. For example, sampling large numbers of microbes ensures that the response of the minority strain will be revealed when the majority strain's growth is inhibited by an antibiotic but the minority strain's growth is not. Such scenarios often arise in real diagnostic situations and patient infections, and it is essential to verify that an antimicrobial mixture inhibits growth of the corresponding set of microbes. The large statistical sampling of the current method provides a significant practical advantage over methods which analyze only single cells or small populations.

An advantage of the microfabricated resonant mass sensors used in some embodiments is that they typically have very small volumes (a nanoliter or less), and measurements consume very small amounts of sample. Typical consumption is less than 100 microlites in a single measurement of a culture, and less than a milliliter in a two hour growth-curve measurement, in which the sample is measured multiple times. Most of the sample is consumed while moving it during the load phase from the sample vial or well to the microchannel.

The methods and systems can be extended beyond bacteria to any living cell or microorganism. For example, the effects of antimicrobials can also be assessed for fungi and protozoans, and the efficacy of more general classes of drugs can be assessed for eukaryotic cells and/or cancerous cells. The effects of other agents on cell growth can also be assessed by this method, including topical anti-infectives and bacteriocides, anti-bacterial soaps, fungicides, and cosmetics. Even more generally, the method can be applied to any particulate entities whose physical characteristics change with time, even non-cellular ones. For example, the aggregation of protein in stressed suspensions of protein molecules is a significant issue in protein therapeutic formulations. The aggregation can be monitored in real time by the repeated sampling and measurement method described herein. Finally, aggregation of inorganic materials may be measured such as occur in many industrial and materials science applications, such as instability and aggregation in colloidal suspensions and aggregation of micro- and nanoscale particles.

The invention claimed is:

1. A method for measuring growth of cells in a fluid culture, comprising;
   a) introducing a first portion of the culture into a microchannel at a first time, the portion of culture having a known fluid volume and containing a plurality of cells at a concentration chosen that for a majority of the time at most one cell is present in the microchannel at a given time,
   b) detecting each cell as the culture passes through the microchannel,
   c) at least one of counting or measuring a property of each cell passing through the microchannel,
   d) introducing at least one additional, different portion of the culture into the microchannel having a known fluid volume at at least one later time,
   e) repeating steps b and c at the later time(s); and, f) calculating the growth rate in the culture from at least one of the change in the count per fluid volume (concentration) or the measured property between the two times, wherein at least one agent, whose effect on the growth rate of the culture is unknown, is added to the culture.

2. The method of claim 1 comprising repeating steps a-f for a plurality (panel) of cultures.

3. The method of claim 1 wherein the microchannel is part of a resonant mass sensor, and the cells' presence affects the resonant behavior of the sensor.

4. The method of claim 1 wherein the microchannel is in view of an optical sensor, and the property measured is a visual parameter.

5. The method of claim 1 wherein the mass of the cells is the property measured.

6. The method of claim 1 wherein the cells are bacteria.

7. The method of claim 1 wherein the cells are fungi.

8. The method of claim 1 wherein the cells are cancer cells.

9. The method of claim 1 wherein the agent comprises at least one of antibiotics, antifungals, or agents used in cancer treatments.

10. The method of claim 1 wherein the times between measurements is greater than time for cells to replicate in a culture not exposed to growth-affecting agents.

11. The method of claim 10 wherein at least one culture portion does not contain a growth-affecting agent, for use as a control.

12. The method of claim 1 wherein at least one measurement/counting step is performed before the agent is added to the culture.

13. The method of claim 1 wherein the agent is added to the culture prior to a measurement/counting step, and within a time before the measurement counting step that is less than the time required for the cells to replicate in the culture.

14. A method for measuring growth of cells in a fluid culture, comprising;
    a) selecting from a panel of vials of varying cultures a first portion of a culture from a vial,
    b) introducing the first portion of the culture into a microchannel at a first time, the portion of culture having a known fluid volume and containing a plurality of cells at a concentration chosen that for a majority of the time at most one cell is present in the microchannel at a given time,
    c) detecting each cell as the culture passes through the microchannel,
    d) at least one of counting or measuring a property of each cell passing through the microchannel,
    e) repeating steps a-d for a plurality of the culture vials in the panel,
    f) repeating steps a-e at least one later time for additional different culture portions having known fluid volumes, and;
    g) calculating the growth rates for the cultures in each vial from at least one of the change in the count per fluid volume (concentration) or the measured property between the two times, wherein at least one agent, whose effect on the growth rate of the culture is unknown, is added to at least one of the cultures.

15. The method of claim 14 wherein at least one of the cultures in the panel is a control with no growth-affecting agent.

16. The method of claim 14 wherein the times between measurements is greater than a known time for the cells to replicate in a culture not exposed to growth-affecting agents.

17. The method of claim 14 wherein the agent(s) are added to at least one culture of the panel before the first measurement/counting step.

18. The method of claim 14 wherein a first agent is added to at least one culture of the panel and a second agent is added to at least one other culture of the panel before the first measurement/counting.

19. A method for measuring growth of cells in a fluid culture, comprising;
    a) selecting from a panel of varying cultures, a first portion of each of a plurality of cultures,
    b) introducing these first portions of the plurality of the cultures into a plurality of microchannels at a first time, each portion of culture having a known fluid volume and containing a plurality of cells at a concentration chosen that for a majority of the time at most one cell is present in the microchannel at a given time where each microchannel accepts the portion from one of the cultures,
    c) detecting each cell in each microchannel as the cultures passes through the microchannels,
    d) at least one of counting or measuring a property of each cell passing through the microchannels,
    e) repeating steps a-d for additional different culture portions having known fluid volumes in the panel,
    f) repeating steps a-e at least one later time, and;
    g) calculating the growth rates for the cultures from at least one of the change in the count per fluid volume (concentration) or the measured property of each culture between the two times, wherein at least one agent, whose effect on the growth rate of the culture is unknown, is added to at least one of the cultures.

20. The method of claim 19 wherein at least one of the cultures in the panel is a control culture with no growth-affecting agent.

21. The method of claim 19 wherein the times between measurements is greater than a known time for the cells to replicate in a culture not exposed to growth-affecting agents.

22. The method of claim 19 wherein the agent(s) are added to at least one culture of the panel before the first measurement/counting step.

23. The method of claim 19 wherein a first agent is added to at least one culture of the panel and a second agent is added to at least one other culture of the panel before the first measurement/counting step.

* * * * *